United States Patent
Mizobuchi et al.

(10) Patent No.: US 6,268,355 B1
(45) Date of Patent: Jul. 31, 2001

(54) STABLE ASPIRIN-CONTAINING PREPARATIONS FOR EXTERNAL USE

(75) Inventors: Noriko Mizobuchi, Kochi; Yuichi Hasegawa, Kakogawa; Mitsuhiro Kawada; Shin-ichi Hisaichi, both of Kagawa-ken, all of (JP)

(73) Assignee: Teikoku Seiyaku Co., Ltd., Kagawa-ken (JP)

( * ) Notice: Subject to any disclaimer, the term of this patent is extended or adjusted under 35 U.S.C. 154(b) by 0 days.

(21) Appl. No.: 09/242,698

(22) PCT Filed: Jun. 23, 1998

(86) PCT No.: PCT/JP98/02780

§ 371 Date: Apr. 26, 1999

§ 102(e) Date: Apr. 26, 1999

(87) PCT Pub. No.: WO98/58651

PCT Pub. Date: Dec. 30, 1998

(30) Foreign Application Priority Data

Jun. 25, 1997 (JP) .................................................. 9-168522

(51) Int. Cl.$^7$ .......................... A61K 31/60; A61K 31/22; A61K 31/225; A61K 31/19

(52) U.S. Cl. .......................... 514/165; 514/546; 514/547; 514/557

(58) Field of Search ..................................... 514/165, 789, 514/557, 546, 547

(56) References Cited

U.S. PATENT DOCUMENTS

| 4,012,508 | 3/1977 | Burton | 424/235 |
|---|---|---|---|
| 4,219,548 | 8/1980 | Reller | 424/234 |
| 4,228,162 | 10/1980 | Luzzi et al. | 424/232 |
| 4,613,498 | 9/1986 | Crosby | 424/154 |
| 4,686,212 | 8/1987 | Ducatman et al. | 514/161 |
| 5,716,636 | 2/1998 | Horstmann et al. | 424/440 |
| 5,861,170 | 1/1999 | Kissel | 424/448 |
| 5,916,918 | * 1/1999 | Konishi | 514/546 |

FOREIGN PATENT DOCUMENTS

| 0784975A1 | 7/1997 | (EP) . |
|---|---|---|
| 469526 | 7/1937 | (GB) . |
| 2144326A | 3/1985 | (GB) . |
| 53-101539A | 9/1978 | (JP) . |
| 56-32425 | 4/1981 | (JP) . |
| 62-89619 | 4/1987 | (JP) . |
| 3-72426A | 3/1991 | (JP) . |
| 4346930 | 12/1992 | (JP) . |
| 5-229949A | 9/1993 | (JP) . |
| 5-246892A | 9/1993 | (JP) . |
| 672879 | 3/1994 | (JP) . |
| 6183980 | 7/1994 | (JP) . |
| 8104624 | 4/1996 | (JP) . |
| 8104625 | 4/1996 | (JP) . |
| 8113531 | 5/1996 | (JP) . |
| 8-208487A | 8/1996 | (JP) . |
| 8333260A | 12/1996 | (JP) . |
| 9503755 | 4/1997 | (JP) . |
| 10-45599A | 2/1998 | (JP) . |
| WO 9312799 | 7/1993 | (WO) . |
| WO 9704759 | 2/1997 | (WO) . |

OTHER PUBLICATIONS

Stozek et al., Stabilization of acetylsalicylic acid solid drug forms. Acta Pol. Pharm, 30(5), 527–532 1973 (see the abstract).*

Database WPI, Section Ch, Week 199621, Derwent Publications Ltd., London, GB; Class A96, AN 1996–205433 XP002124811 & JP 08 073346 A (Sekisui Chem Ind Co Ltd), Mar. 19, 1996.

Database WPI, Section Ch, Week 198818, Derwent Publications Ltd., London, GB; Class A96, AN 1988–123655 XP002124812 & JP 63 068528 A (Meiji Seika Kaisha), Mar. 28, 1988.

Masatoshi Tsuchiya, Journal of the Nippon Hospital Pharmacists Association, vol. 20, No. 6 (1994), pp. 502–508.

* cited by examiner

*Primary Examiner*—Kevin E. Weddington
(74) *Attorney, Agent, or Firm*—Birch, Stewart, Kolasch & Birch LLP

(57) ABSTRACT

External preparations containing Aspirin which are stored for a long term and superior in dermal absorbability.

The preparations are prepared by mixing Aspirin together with at least one substance selected from an ester of an organic acid ester having 2 to 20 carbon atoms, a glycerol fatty acid ester, silicon oil, hydrocarbon oil and crotamiton.

7 Claims, 1 Drawing Sheet

STABLE ASPIRIN-CONTAINING PREPARATIONS FOR EXTERNAL USE

DESCRIPTION

A stable external preparation containing Aspirin

TECHNICAL FIELD

The present invention relates to a stable external preparation containing Aspirin (acetyl salicylic acid).

More specifically, the present invention relates to a technique to store stably an external preparation containing Aspirin for a long term which is characterized in mixing Aspirin together with at least one substance selected from an ester of an organic acid having 2 to 20 carbon atoms, a glycerol fatty acid ester, silicon oil, hydrocarbon oil and crotamiton.

BACKGROUND ART

Aspirin has been used as an anti-inflammatoric antipyretic analgesics from of old. It is in general orally administered in form of tablets, granules and so on.

However, due to the intestinal injury by Aspirin, its external application has been recently studied. The results are reported in Japanese Patent Pub. No. 3-72426, in Japanese Patent Pub. No. 6-72879, in Japanese Patent Pub. 6-183980, in Japanese Patent Pub. No. (Tokuhyo Hei) 9-503755, etc.

These techniques are; one which makes weight on transdermal absorption and does not take care of stability of Aspirin; one which secures stability of Aspirin for a short term, but was not necessarily satisfied for a long term stability; a method characterized in patches to be consumed once and very difficult to apply to preparations consisting of a pack which are often opened and closed, for example creams, solutions, etc.; such a case as in application to preparations, such as ointments, due to the presence of crystals the feeling on use is extremely bad and there is irritation by roughness and therefore, it is very difficult to apply to the region of injured skin like heat injuries. There are many points to be improved in these techniques.

Furthermore, there are disclosed techniques of patches containing Aspirin in Japanese Patent Pub. Nos. 8-104624, 8-104625 and 8-113531, but there are not disclosed techniques to stabilize Aspirin in the patches for a long term.

The literatures which describe methods for stabilization of Aspirin in preparations except for external preparations, are Japanese Patent Pub. No.56-32425, Japanese Patent Pub. No. 62-89619, Japanese Patent Pub. No. 4-346930 and so on.

Because Aspirin is readily hydrolyzed even in the presence of small amount of water and furthermore, by depending on a kind of additives the hydrolysis is accelerated, in these literatures in order to avoid to contact with the additive, it is disclosed to use the protective layer consisting of sucrose, or to use binders in which water was excluded as much as possible and to add a hydrogenated oil as a lubricant. However, it is hardly possible to apply such a technique to external preparations. For example, it is very difficult to make a protective layer between Aspirin and a base in ointments.

As such, in external preparations of Aspirin, the technique to avoid water to the possible extent in preparations and store in the package in which water is eliminated as much as possible in order to secure stability of Aspirin in preparing external preparations are found, but the technique to be applied to all external preparations and to secure the satisfied stability has not been shown.

DISCLOSURE OF INVENTION

The present invention was made in considering of the above problems and the object of the present invention is to provide an external preparation containing Aspirin which is superior in stability and transdermal absorption and can be stored for a long term.

That is, by mixing Aspirin together with at least one substance selected from an ester of an organic acid having 2 to 20 carbon atoms, a glycerol fatty acid ester, silicon oil and hydrocarbon oil, it was found to solve the above problems and thus, the present invention was completed.

The amount of Aspirin as an active ingredient in an external preparation of the present invention is 0.001 to 30% by weight per total amount, preferably 0.01 to 20% by weight, more preferably 0.05 to 15% by weight. In case of more than 30% by weight of Aspirin, it causes hydrolysis of Aspirin due to increase of stabilization effect by the stabilizing agent. On the other hand, in case of less than 0.001 percent by weight of Aspirin it is hardly to exhibit the pharmacological activities of Aspirin. Each case is not preferable.

The stabilizing agents of the present invention are selected from substances having ability to dissolve Aspirin, too and for example, an ester of an organic acid having 2 to 20 carbon atoms, a glycerol fatty acid ester, silicon oil, hydrocarbon oil and crotamiton are used, and in general one substance or more selected from them are used.

Examples of the organic acids of esters of organic acids having 2 to 20 carbon atoms are myristic acid, lauric acid, oleic acid, sebacic acid, palmitic acid, caprylic acid, isooctanoic acid, stearic acid, isostearic acid, acetic acid, propionic acid, isopalmitic acid, undecylic acid, linoleic acid, linolenic acid, adipic acid, salicylic acid, benzoic acid, lactic acid, caproic acid, eicosanic acid, etc., preferably myristic acid, oleic acid, sebacic acid, palmitic acid, isooctanoic acid, isostearic acid and adipic acid, more preferably myristic acid, oleic acid, sebacic acid and adipic acid. Examples of the esters of the organic acids are esters with an aliphatic monoalcohol, such as methyl ester, ethyl ester, propyl ester, isopropyl ester, butyl ester, hexyl ester, octyl ester, decyl ester, cetyl ester, isocetyl ester, stearyl ester, isostearyl ester, oleyl ester, etc.

Examples of the glycerol fatty acid esters are a plant oil, such as soy bean oil, almond oil, sesame oil, olive oil, camellia oil, corn oil, coconuts oil, etc., an animal oil, such as whale oil, lard, beef tallow, lever oil, etc., triacetin (glycerol triacetate), a middle chain-fatty acid triglyceride, glycerol triisooctanoate, etc., preferably soy bean oil, almond oil, sesame oil, triacetin, a middle chain-fatty acid triglyceride and glycerol triisooctanoate, more preferably soy bean oil, almond oil and a middle chain-fatty acid triglyceride.

Examples of the hydrocarbon oils are liquid paraffin, squalane, squalene, etc., preferably liquid paraffin and squalane.

The stabilizing agents of the present invention do not only stabilize Aspirin, but also dissolve Aspirin. Therefore, in mixing the stabilizing agent in external preparations, it has enhancing effect of absorption of Aspirin from skin and it is very preferable.

The amount of the stabilizing agent is preferably 0.1 to 20 times as much as the amount of Aspirin, more preferably 0.5 to 15 times. In case of less than 0.1 time, Aspirin can not dissolve thoroughly and as a result, transdermal absorption enhancing activity is prohibited. On the other hand in case of more than 20 times irritation against skin etc. occurs. The amount of the stabilizing agent per total weight depends on form of the preparations, but is preferably 0.01 to 50% by weight. When using the stabilizing agent more than 50% by weight in plasters it is difficult to keep their form, and in cataplasms or creams the separation from hydrophilic substances etc. and skin irritation occur and it is not desirable. In case of less than 0.01% by weight especially in the preparation in which water is added, it is difficult to secure stability of Aspirin.

In order to avoid hydrolysis of Aspirin to the possible extent in the preparation of the present invention, it should be taken care for water contents. For example it is desirable not to add water, or even in case of addition of water the amount of water per total weight is desirably less than 10%, more desirably less than 5%. Within this range the stabilization effect of Aspirin by the stabilizing agent is exhibited and it is possible to avoid hydrolysis of Aspirin. When the amount of water to be added is beyond 10% by weight, the stabilization effect of Aspirin by the stabilization agent is not exhibited enough and hydrolysis of Aspirin is accelerated and therefore, it is not desirable. Kinds of the preparations containing Aspirin of the present invention are not limited if these are usually used as external preparations, such as cataplasms, plasters, ointments, creams, external powders, etc.

As the other ingredients except for the stabilizing agents of the present invention there can be used ones which are used in ordinal external preparations. However, substances which prohibit stability of Aspirin should be avoided or be used at least.

In case of cataplasms, Aspirin and the stabilizing agent are added to a following adhesive gel base to prepare cataplasms; an adhesive gel base containing 4 to 20% by weight of a tackifier such as polyacrylic acid, polyacryl acid copolymer, etc., 1 to 5% by weight of a crosslinker, such as aluminum sulfate, aluminum potassium sulfate, aluminum chloride, aluminum magnesium metasilicate, dihydroxyalminum acetate, etc., 1 to 15% of a viscosity increaser, such as sodium polyacrylate, polyvinyl alcohol, polyvinylpyrrolidone, gelatin, sodium alginate, etc., and 30 to 80% by weight of a polyhydric alcohol, such as glycerin, polyethlene glycol (macrogol), propylene glycol, 1,3-butanediol, etc. Furthermore, in the adhesive gel base there may be mixed a surfactant, such as a polyoxyethylene derivative etc., a perfume, such as 1-menthol etc., a preservative, such as a p-hydroxybenzoate etc., small amount of water, etc.

In case of plasters, Aspirin and the stabilizing agent are added to a following adhesive base material to prepare plasters; an adhesive base material containing 20 to 40% by weight of a tacking agent, such as a stylene-isoprene-stylene block copolymer, an acrylate resin, etc., 25 to 45% by weight of a tackifier resin, such as a cyclic saturated hydrocarbon, a hydrogenated rosin, etc., 5 to 30% by weight of a softening agent, such as liquid gum etc., and 1 to 5% of an antioxidant, such as dibutyl hydroxytoluene etc. And 0.1 to 5% by weight of a high molecular compound being able to contain water, such as polyacrylic acid sodium, polyvinylalcohol, and small amount of water may be added to the above adhesive base material to prepare plaster containing water. Furthermore, a polyhydric alcohol, such as propylene glycol etc., an absorption promoter, such as oleic acid etc., and a surfactant, such as a polyoxyethylene derivative etc. may be mixed to them.

In case of ointments or creams, Aspirin and the stabilizer are added to 30 to 99.8% by weight of a base, such as white vaseline (petroleum), yellow vaseline (petroleum), lanolin, purified bee wax, cetanol, stearyl alcohol, a hydrogenated oil, hydrocarbon gel, polyethylene glycol, etc. to prepare ointments, and further 0.1 to 7% by weight of a surfactant, such as sorbitan sesquioleate, glycerol monostearate, polysorbate 80, etc., and small amount of water are mixed to them to prepare creams. These preparations may contain an antioxidant, such as a tocopherol derivative etc., and a preservative, such as a p-hydroxybenzoic acid ester etc.

In case of external powders, the preparations are prepared by mixing 50 to 99.8% by weight of a filler, such as potato starch, rice starch, corn starch, talc, zinc oxide, etc. with Aspirin and the stabilizing agent.

The external preparations containing Aspirin of the present invention are prepared according to the conventional methods of external preparations. For example, ointments are prepared by melting a base and the stabilizing agent under warming, mixing them homogeneously and, if necessary adding an additive, such as an antioxidant, a preservative, a surfactant, purified water, etc., and then, adding powdered Aspirin under stirring.

Cataplasms are prepared by dissolving a tackfier, such as polyacrylic acid etc. and a viscosity increaser in a polyhydric alcohol, such as glycerin etc. by heating, adding Aspirin, the stabilizing agent and another additive after cooling, mixing them homogeneously and then adding a crosslinker to prepare adhesive gel bases. Then, by spreading the bases thus obtained on adequate support like felt and cutting it in desired size, there are prepared cataplasms.

The plasters are prepared as follows; by mixing a tacking agent, such as acrylate etc., a tackifier resin, such as a hydrogenated rosin, etc., a softener, such as liquid gum etc. and, if desired an antioxidant under stirring and by heating: and adding a mixture of Aspirin and a stabilizing agent prepared separately and kneading: and then spreading on release paper: and after drying laminating with a soft support, such as polyurethane film, polyethylene film, vinyl chloride film, woven textile, felt, etc.: and cutting it in desired size.

BEST MODE FOR CARRYING OUT THE INVENTION

Figure 1:
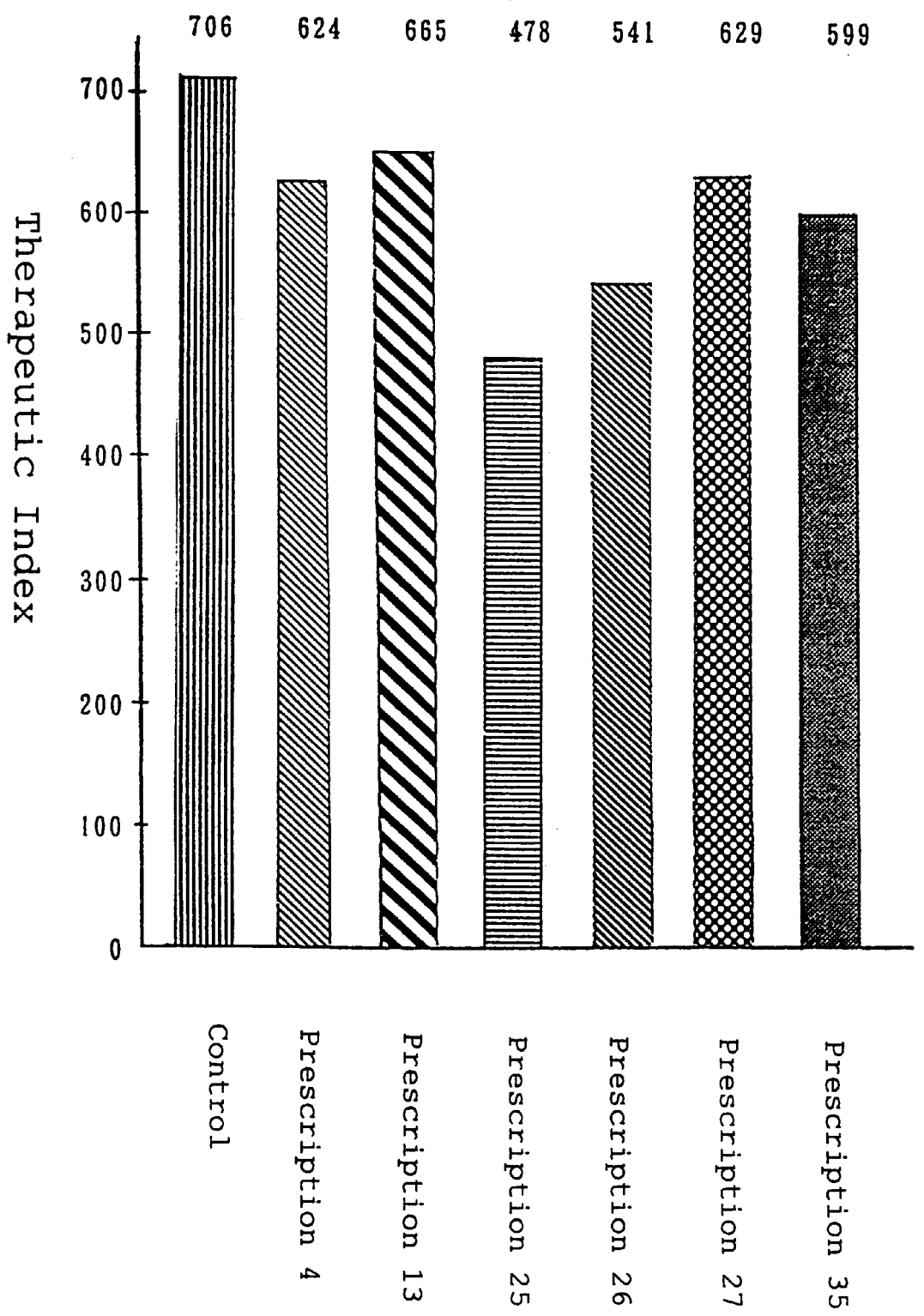
FIG. 1. shows the activity of ointments containing Aspirin against dermal coloboma of rats.

The present invention is shown in more detail by the following examples. But the present invention is not limited by the examples.

EXAMPLE 1 TO 7

OINTMENTS

According to the ingredients shown in Table 1, white vaseline or hydrocarbon gel and a stabilizing agent(s) were melted under warming on a water bath. Thereto Aspirin was added and the mixture was well stirred to disperse Aspirin and further cooled under stirring to prepare ointments. In this procedure there are used machines, such as a vacuum emulsifier (T.K.ROBO MIXER prepared by Tokusyukika Kogyo), a grinder, a planetary mixer, etc.

TABLE 1

Ingredients of ointments containing Aspirin

| Example | 1 | 2 | 3 | 4 | 5 | 6 | 7 |
|---|---|---|---|---|---|---|---|
| Ingredient | | | ingredient ratio (% by weight) | | | | |
| White vaseline | 97 | 94 | 98.4 | | | | 50 |
| Hydrocarbon gel | | | | 94.5 | 96 | 60 | 49.8 |
| Aspirin | 0.5 | 5 | 0.1 | 0.5 | 0.5 | 15 | 0.01 |
| Isopropyl myristate | | | | 2.5 | 1 | 25 | |
| Squalane | | | 1.5 | | | | |
| Sesame oil | 2.5 | | | | | | |
| Silicon oil | | 1 | | | | | |
| Crotamiton | | | | 2.5 | 2.5 | | 0.19 |

EXAMPLES 8–14

CREAMS

According to the ingredients shown in Table 2, white vaseline, yellow vaseline or hydrocarbon gel and a stabilizing agent(s) were melted under warming on a water bath. Thereto Aspirin was added and the mixture was well stirred to disperse Aspirin. On the other hand a surfactant was added to purified water and the solution was stirred well. This solution was added to the dispersion containing Aspirin prepared above. The mixture was stirred and cooled to prepare creams. In this procedure a vacuum emulsifier (T.K.ROBO MIXER prepared by Tokusyukika Kogyo) was used.

TABLE 2

Ingredients of creams containing Aspirin

| Example | 8 | 9 | 10 | 11 | 12 | 13 | 14 |
|---|---|---|---|---|---|---|---|
| Ingredient | | | ingredient ratio (% by weight) | | | | |
| Hydrocarbon gel | | 59 | | | | | |
| White vaseline | 85 | | 30 | 40 | 35 | 97.45 | 45 |
| Yellow vaseline | | | 24 | | | | |
| Cetanol | | | | | | | 10 |
| Aspirin | 0.5 | 5 | 2 | 5 | 5 | 0.5 | 5 |
| Isopropyl myristate | 10 | 30 | | | | | |
| Glycerin trioctanoate | | | 40 | 45 | 45 | 0.05 | 30 |
| Polysorbate 80 | 0.5 | 1 | | | | | |
| Glycerin monostearate | | | 2 | 5 | 5 | 1 | |
| Sorbitan sesquioleate | | | | | | | 5 |
| Purified water | 4 | 5 | 2 | 5 | 10 | 1 | 5 |

EXAMPLE 15–20

PLASTERS

According to ingredients shown in Table 3, a stylene-isoprene-stylene block copolymer, a cyclic satulated hydrocarbon resin, a liquid gum (polybutene, polyisoprene gum), an antioxidant (dibutylhydroxytoluene), or liquid paraffin was put in a warmed kneader and melted under heating with stirring. On the other hand, Aspirin, isopropyl myristate and a hydrogenated rosin glycerin ester were mixed and stirred and the mixture was added to the mixture prepared previously and kneaded well under stirring.

In cases of Examples 15 to 18, adhesives prepared thus, were spread on an appropriate support and cut in desired size to prepare plasters containing Aspirin. In cases of Examples 19 and 20, sodium polyacrylate was dissolved in warmed purified water under stirring. This solution was added to oil tackfiers prepared above and the mixture was stirred homogeneously, and then were spread on an appropriate support and cut in desired size to prepare plasters containing Aspirin.

TABLE 3

Ingredients of plasters containing Aspirin

| Example | 15 | 16 | 17 | 18 | 19 | 20 |
|---|---|---|---|---|---|---|
| Ingredient | | | ingredient ratio (% by weight) | | | |
| Aspirin | 2.5 | 10 | 15 | 5 | 5 | 5 |
| stylene-isoprene-stylene block copolymer | 30 | 30 | 25 | 35 | 25 | 30 |
| hydrogenated rosin glycerin ester | | 40 | 40 | 40 | | |
| Polybutene | | 9 | | 5 | | |
| Polyisoplene gum | 10 | | 10 | | | |
| Dibutyl hydroxytoluene | 1 | 1 | 1 | 1 | | |
| Liquid paraffin | 10 | | | | 15 | 20 |
| Isopropyl myristate | 5 | 10 | 9 | 14 | 10 | 15 |
| cyclic saturated hydrocarbon | 41.5 | | | | 38.5 | 27.5 |
| Sodium polyacrylate | | | | | | 0.5 |
| Polyvinyl alcohol | | | | | 1.5 | |
| Purified water | | | | | 5 | 2 |

EXAMPLES 21 TO 27

CATAPLASMS

Polyacrylic acid and polyvinylpyrrolidone were dispersed and then dissolved in propylene glycol, Macrogol 200, Macrogol 400, or 1,3-butanediol under warming. Separately, Aspirin was dispersed and dissolved in isopropyl myristate, crotamiton, or caster oil and this solution was added to the base solution prepared above and kneaded and then, thereto aluminum magnesium metesilicate or polysorbate 80 was added and kneaded. The resulting adhesive was spread on an appropriate support like felt to prepare cataplasms containing Aspirin.

TABLE 4

Ingredients of cataplasms containing Aspirin

| Example | 21 | 22 | 23 | 24 | 25 | 26 | 27 |
|---|---|---|---|---|---|---|---|
| Ingredient | | | | ingredient ratio (% by weight) | | | |
| Aspirin | 5 | 1 | 10 | 0.5 | 0.1 | 25 | 5 |
| Isopropyl myristate | 10 | 4 | 10 | 4.5 | 0.4 | | 5 |

TABLE 4-continued

Ingredients of cataplasms containing Aspirin

| Example | 21 | 22 | 23 | 24 | 25 | 26 | 27 |
|---|---|---|---|---|---|---|---|
| Ingredient | ingredient ratio (% by weight) | | | | | | |
| Crotamiton |  | 5 | 5 | 5 | 0.5 | 5 |  |
| Polyacrylic acid | 15 | 15 | 5 | 10 | 9 | 10 | 10 |
| Glycerin | 20 | 20 | 13 | 40 | 10 | 12 | 23 |
| Propyleneglycol | 30 | 30 | 20 |  | 20 |  |  |
| Macrogol 200 |  | 5 |  | 25 | 20 |  |  |
| Macrogol 400 | 10 | 10 |  | 10 |  | 10 | 25 |
| 1,4-Butanediol |  |  | 10 |  | 27.5 | 15 |  |
| aluminum magnesium metesilicate | 3 | 3 | 2 | 1 | 2 | 3 | 2 |
| Polyvinyl pyrolidone | 5 | 5 | 10 | 3 | 10 | 5 | 5 |
| Castor oil |  |  | 10 |  |  |  | 10 |
| Polysorbate 80 | 2 | 2 | 5 | 1 | 0.5 | 5 | 5 |

EXAMPLES 28 TO 32

EXTERNAL POWDERS

Aspirin and isopropyl myristate, soy bean oil, or liquid paraffin were mixed well and the mixture was added to potato starch, corn starch, talc or zinc oxide and to mix homogeneously. There were thus obtained external powders containing Aspirin.

TABLE 5

Ingredients of external powders containing Aspirin

| Example | 28 | 29 | 30 | 31 | 32 |
|---|---|---|---|---|---|
| Ingredient | ingredient ratio (% by weight) | | | | |
| Aspirin | 5 | 20 | 0.50 | 0.5 | 25 |
| Isopropyl myristate | 5 |  | 2.5 |  | 5 |
| Soybean oil |  | 10 |  |  | 5 |
| Liquid paraffin |  |  |  | 4.5 | 5 |
| Potato starch | 30 |  |  | 25 | 30 |
| Corn starch | 20 | 30 | 47 |  |  |
| Talc | 40 | 40 |  | 50 | 30 |
| Zinc oxide |  |  | 50 | 20 |  |

COMPARATIVE EXAMPLE 1

According to the ingredients shown in below, white vaseline and isostearic acid were melted under warming on a water bath. Thereto Aspirin was added and the mixture was stirred to disperse well and cooled to prepare an ointment. In this procedure a vacuum emulsifier (T.K.ROBO MIXER prepared by Tokusyukika Kogyo) was used.

| Ingredients | Contents |
|---|---|
| Aspirin | 0.5 g |
| White vaseline | 97.0 g |
| Isostearic acid | 2.5 g |

COMPARATIVE EXAMPLES 2

According to the method and ingredients described in Comparative Example 1 except for oleyl alcohol instead for isostearic acid to prepare an ointment.

COMPARATIVE EXAMPLE 3

According to the method and ingredients described in Comparative Example 1 except for benzyl alcohol instead for isostearic acid to prepare an ointment.

COMPARATIVE EXAMPLE 4

According to the following ingredients, Aspirin was dissolved in a small amount of ethanol and the solvent was distilled off to prepare fine powders. Thereto were added polysorbate 80 and hydrocarbon gel and the mixture was mixed homogeneously to prepare an ointment.

| Ingredients | Contents |
|---|---|
| Aspirin | 0.5 g |
| Hydrocarbon gel (Japanese Pharmaceutical Excipients) | 94.5 g |
| Polysorbate 80 | 5.0 g |

COMPARATIVE EXAMPLE 5

According to the following ingredients, Aspirin, hydrocarbon gel and carnauba wax were mixed homogeneously to prepare an ointment.

| Ingredients | Contents |
|---|---|
| Aspirin | 0.5 g |
| Hydrocarbon gel (Japanese Pharmaceutical Excipients) | 98.5 g |
| Carnauba wax | 5.0 g |

EXPERIMENT 1

The ointments of present invention prepared based on prescriptions 1 to 42 shown in Tables 6–8, and the ointments prepared by Comparative Examples 1 to 4 were tested on stability in storage at 75% RH at 40° C., and at 50° C. Test samples were stored under each condition for one or two months, and after sampling, contents of Aspirin remaining in each sample was measured and the remaining percentage per initial content was calculated and shown in Table 9–10.

As shown in Tables 9 and 10, when preparations of Comparative Examples were stored for 2 months at 40° C. and 50° C., in case of the former, at least about 20% of Aspirin was decomposed and in case of the latter almost of Aspirin was decomposed. On the contrast when preparations containing the stabilizing agent of the present invention were stored at the same conditions, at least 93% of Aspirin remains at 40° C. and about 70% of Aspirin remains even at 50° C. Accordingly, it is found that preparations of the present invention show excellent stability effect to Aspirin in comparison with preparations of Comparative Examples.

EXPERIMENT 2

The cream prepared by example 14, the plasters prepared by Examples 16 and 18, and the external powder prepared by Example 29 were tested on stability in storage at 75% RH at 40° C. in the same manner as Experiment 1. Content of Aspirin was measured and the results were shown in Table 11.

EXPERIMENT 3

By using the ointments of the present invention prepared based on prescriptions No. 18, 20, 25, 27, 28, 30, 32, 33, 34, 35, 36, 37, 39, 40 and 41 shown in Tables 6 to 8, and the ointments prepared by Comparative Examples 4 and 5, in vitro skin-permeability test was carried out. Abdominal skin of Wistar rat (6 weeks old) was taken out and after removal of its subcutaneous fat was fixed on a Frantsu type expansion cell (cell volume of a receiver: 10 cm$^3$, effective expansion surface area: 2.27 cm$^2$). A phosphate buffer solution (pH 7.2) was filled in the receiver and ointments (100 mg) were spread on the side of the corium. Four, 8 and 24 hours after the spread, the solution in the receiver was taken and amounts of Aspirin and salicylic acid in it were measured. The amount of salicylic acid was calculated into amount of Aspirin. Both amounts were combined and divided by the amount of Aspirin contained in the ointment and multiplied by 100 and its values were shown in Table 12.

As shown in Table 12, in cases of the preparations of Comparative Examples maximum skin permeation rate was at most about 20%, but in case of the ointment of the present invention using a stabilizing agent(s), its permeation rate was at least 20% and in some cases more than 70% and therefore, the ointment of the present invention is superior to that of the Comparative Example in the skin permeation.

EXPERIMENT 4

The activity of ointments containing Aspirin on the skin injured rats.

A group consisting of 6 Wistar rats (400–450 g) was used. After removal of hairs on back on the rat, the back sterilized by Isodine® (popidone-iodine) and the skin of the back was punched out by a round punch (inner diameter: 12 mm) under anesthesia by ether to make two parts of injuries symmetrically with respect to mesad. From one day after making the injuries ointments prepared based on prescriptions 1, 18, 30, 31, 31 and 40 were applied to the injuries 0.2 g per injury part once a day for 14 days. The control group was not treated. The judgment of the effect was done as follows: The major axis and the miner axis on the injury were measured and calculate the area and change of the areas was calculated by the following formula to prepare a curve of the area changing. The area under the thus obtained curve was calculated and its value was as index (therapeutic index). The result was shown in FIG. 1.

As is clear from FIG. 1, it is shown that the ointment using a stabilizing agent of the present invention shows therapeutic effect against skin injury of rats.

Change of the area =[major axis ×miner axis of the injury on the observation date] / [major axis ×miner axis of a injury on one day after preparing the injury) ×100

TABLE 6

Prescription of ointments containing Aspirin

| Ingredients | ratio of ingredients (% by weight) | | | | | | |
|---|---|---|---|---|---|---|---|
| Example of prescription | 1 | 2 | 3 | 4 | 5 | 6 | 7 |
| White vaseline | 97 | 97 | 97 | 97 | 97 | 97 | 97 |
| Aspirin | 0.5 | 0.5 | 0.5 | 0.5 | 0.5 | 0.5 | 0.5 |
| Diethyl sebacinate | 2.5 | | | | | | |
| Myristyl myristate | | 2.5 | | | | | |
| Cetyl parmitate | | | 2.5 | | | | |
| Isopropyl myristate | | | | 2.5 | | | |
| Glycerol triisooctanoate | | | | | 2.5 | | |
| Isostealyl palmitate | | | | | | 2.5 | |
| Oleyl oleate | | | | | | | 2.5 |

TABLE 6-continued

Prescription of ointments containing Aspirin

| Ingredients | ratio of ingredients (% by weight) | | | | | | |
|---|---|---|---|---|---|---|---|
| Example of prescription | 8 | 9 | 10 | 11 | 12 | 13 | 14 |
| White vaseline | 97 | 97 | 97 | 97 | 97 | 97 | 97 |
| Aspirin | 0.5 | 0.5 | 0.5 | 0.5 | 0.5 | 0.5 | 0.5 |
| Cetyl isooctanoate | 2.5 | | | | | | |
| Isocetyl isostearate | | 2.5 | | | | | |
| Isopropyl parmtate | | | 2.5 | | | | |
| Octyldodecyl myristate | | | | 2.5 | | | |
| Squalane | | | | | 2.5 | | |
| Soybean oil | | | | | | 2.5 | |
| Sesame oil | | | | | | | 2.5 |

TABLE 7

Prescription of ointments containing Aspirin

| Ingredients | ratio of ingredients (% by weight) | | | | | | |
|---|---|---|---|---|---|---|---|
| Example of prescription | 15 | 16 | 17 | 18 | 19 | 20 | 21 |
| White vaseline | 97 | 97 | 97 | 97 | 97 | 97 | 97 |
| Aspirin | 0.5 | 0.5 | 0.5 | 0.5 | 0.5 | 0.5 | 0.5 |
| Sweet almond oil | 2.5 | | | | | | |
| Silicon oil | | 2.5 | | | | | |
| Liquid palaffin | | | 2.5 | | | | |
| Crotamiton | | | | 2.5 | | | |
| middle chain-fatty acid triglyceride | | | | | 2.5 | | |
| Diisopropyl adipinate | | | | | | 2.5 | |
| Triacetin | | | | | | | 2.5 |

| Example of prescription | 22 | 23 | 24 | 25 | 26 | 27 | 28 |
|---|---|---|---|---|---|---|---|
| White vaseline | 97 | 97 | 97 | | | | |
| Hydrocarbon gel | | | | 98.5 | 98 | 97.5 | 97 |
| Aspirin | 0.5 | 0.5 | 0.5 | 0.5 | 0.5 | 0.5 | 0.5 |
| Diisopropyl cebacinate | 2.5 | | | | | | |
| n-Butyl acetate | | 2.5 | | | | | |
| Hexyl laurate | | | 2.5 | | | | |
| Crotamiton | | | | 1 | 1.5 | 2.0 | 2.5 |

TABLE 8

Prescription of ointments containing Aspirin

| Ingredients | ratio of ingredients (% by weight) | | | | | | |
|---|---|---|---|---|---|---|---|
| Example of prescription | 29 | 30 | 31 | 32 | 33 | 34 | 35 |
| Hydrocarbon gel | 97 | 94.5 | 94.5 | 94.5 | 94.5 | 94.5 | 94.5 |
| Aspirin | 0.5 | 0.5 | 0.5 | 0.5 | 0.5 | 0.5 | 0.5 |
| Isopropyl myristate | 2.5 | | | | | | |
| Crotamiton | | 5 | | | | | |
| Isopropyl myristate | | | 5 | | | | |
| Oleyl oleate | | | | | 5 | | |
| Diisopropyl cebacinate | | | | | | 5 | |

TABLE 8-continued

Prescription of ointments containing Aspirin

| Ingredients | ratio of ingredients (% by weight) | | | | | | |
|---|---|---|---|---|---|---|---|
| Diisopropyl adipinate | | | | | 5 | | |
| middle chain-fatty acid triglyceride | | | | | | 5 | |
| Example of prescription | 36 | 37 | 38 | 39 | 40 | 41 | 42 |
| Hydrocarbon gel | 94.5 | 94.5 | 94.5 | 94.5 | 94.5 | 94.5 | 94.5 |
| Aspirin | 0.5 | 0.5 | 0.5 | 0.5 | 0.5 | 0.5 | 0.5 |
| Octyldodecyl myristate | 5 | | | | | | |
| Sesame oil | | 5 | | | | | |
| Soybean oil | | | 5 | | | | |
| Squalane | | | | 5 | | | |
| Glycerol trioctanoate | | | | | 5 | | |
| Isopropyl myrystate | | | | | | 1 | 2.5 |
| Crotamiton | | | | | | 2.5 | 2.5 |

TABLE 9

Test results on stability of ointments containing Aspirin

| | 40° C. 75% RH | | | 50° C. 75% RH | | |
|---|---|---|---|---|---|---|
| | Remain ratio (%) | | | | | |
| Prescription | Initial | 1 month | 2 month | Initial | 1 month | 2 month |
| 1 | 100 | 96.0 | 93.8 | 100 | 90.7 | 81.9 |
| 2 | 100 | 99.6 | 99.3 | 100 | 98.4 | 97.6 |
| 3 | 100 | 98.4 | 97.5 | 100 | 95.6 | 93.3 |
| 4 | 100 | 98.5 | 96.4 | 100 | 95.6 | 86.1 |
| 5 | 100 | 99.0 | 98.9 | 100 | 97.5 | 95.6 |
| 6 | 100 | 98.3 | 94.0 | 100 | 95.3 | 89.8 |
| 7 | 100 | 98.6 | 98.0 | 100 | 94.6 | 81.0 |
| 8 | 100 | 99.8 | 99.6 | 100 | 97.5 | 96.4 |
| 9 | 100 | 99.0 | 98.6 | 100 | 96.3 | 92.5 |
| 10 | 100 | 99.2 | 98.8 | 100 | 94.9 | 91.9 |
| 11 | 100 | 98.6 | 97.9 | 100 | 93.4 | 91.0 |
| 12 | 100 | 99.5 | 99.3 | 100 | 98.0 | 96.2 |
| 13 | 100 | 99.6 | 98.2 | 100 | 96.2 | 92.3 |
| 14 | 100 | 99.8 | 98.6 | 100 | 98.5 | 97.5 |
| 15 | 100 | 98.5 | 96.7 | 100 | 96.0 | 90.0 |
| 16 | 100 | 99.5 | 99.0 | 100 | 99.1 | 97.7 |
| 17 | 100 | 99.1 | 99.0 | 100 | 98.3 | 96.8 |
| 18 | 100 | 97.5 | 94.8 | 100 | 88.1 | 80.7 |
| 19 | 100 | 99.7 | 99.4 | 100 | 98.3 | 97.2 |
| 20 | 100 | 99.6 | 99.6 | 100 | 96.7 | 95.1 |
| 21 | 100 | 93.5 | 88.9 | 100 | 88.3 | 71.6 |
| 22 | 100 | 99.4 | 98.5 | 100 | 98.0 | 95.6 |
| 23 | 100 | 99.5 | 98.7 | 100 | 96.8 | 95.1 |
| 24 | 100 | 99.0 | 97.3 | 100 | 95.8 | 93.3 |

TABLE 10

Test results on stability of ointments containing Aspirin

| | 40° C. 75% RH | | | 50° C. 75% RH | | |
|---|---|---|---|---|---|---|
| | Remain ratio (%) | | | | | |
| Prescription | Initial | 1 month | 2 month | Initial | 1 month | 2 month |
| 25 | 100 | 98.1 | 97.4 | 100 | 90.1 | 89.0 |
| 26 | 100 | 97.1 | 93.4 | 100 | 96.5 | 89.9 |
| 27 | 100 | 96.3 | 93.9 | 100 | 84.4 | 78.3 |
| 28 | 100 | 97.4 | 95.9 | 100 | 94.4 | 84.6 |
| 29 | 100 | 99.2 | 99.2 | 100 | 98.8 | 96.6 |
| 30 | 100 | 94.6 | 90.0 | 100 | 88.5 | 79.1 |
| 31 | 100 | 98.7 | 95.9 | 100 | 95.4 | 93.6 |
| 32 | 100 | 98.7 | 97.0 | 100 | 96.1 | 94.9 |
| 33 | 100 | 97.9 | 96.8 | 100 | 93.5 | 90.7 |
| 34 | 100 | 99.3 | 98.8 | 100 | 94.5 | 89.3 |
| 35 | 100 | 100.0 | 99.8 | 100 | 96.5 | 94.8 |
| 36 | 100 | 99.9 | 97.0 | 100 | 96.6 | 93.9 |
| 37 | 100 | 98.4 | 97.9 | 100 | 96.1 | 94.2 |
| 38 | 100 | 99.0 | 97.6 | 100 | 94.7 | 93.1 |
| 39 | 100 | 99.0 | 98.2 | 100 | 97.2 | 95.6 |
| 40 | 100 | 99.2 | 98.2 | 100 | 96.7 | 94.5 |
| 41 | 100 | 97.7 | 96.6 | 100 | 90.8 | 86.5 |
| 42 | 100 | 96.3 | 93.8 | 100 | 87.2 | 82.7 |
| Comp Ex. 1 | 100 | 84.9 | 80.8 | 100 | 80.7 | 54.7 |
| Com. Ex. 2 | 100 | 66.1 | 46.0 | 100 | 1.1 | 0 |
| Com. Ex. 3 | 100 | 61.4 | 28.5 | 100 | 2.8 | 0 |
| Com. Ex. 4 | 100 | 20.4 | 11.4 | 100 | 0 | 0 |

TABLE 11

The test results on stability of preparations containing Aspirin

| | Remain ratio of (%) | | |
|---|---|---|---|
| | Initial | 1 month | 2 month |
| Example 14 (cream) | 100 | 89.1 | 74.7 |
| Example 16 (plaster) | 100 | 94.3 | 90.2 |
| Example 18 (plaster) | 100 | 89.3 | 79.3 |
| Example 29 (external powder) | 100 | 96.6 | 90.1 |

TABLE 12

The results of measurement on in vitro skin permeability of Aspirin

| | 4 hours later | 8 hours later | 24 hours later |
|---|---|---|---|
| Prescription No. | Permeability (%) | | |
| 18 | 5.8 | 12.2 | 24.7 |
| 20 | 0.7 | 6.6 | 23.4 |
| 25 | 7.9 | 14.9 | 33.4 |
| 27 | 10.7 | 20.4 | 42.8 |
| 28 | 14.5 | 26.7 | 53.6 |
| 30 | 4.7 | 11.6 | 36.4 |
| 32 | 7.8 | 13.4 | 44.9 |
| 33 | 7.7 | 15.8 | 47.3 |
| 34 | 3.8 | 10.9 | 34.6 |
| 35 | 5.2 | 6.3 | 28.4 |
| 36 | 3.9 | 15.4 | 37.6 |
| 37 | 2.5 | 5.9 | 24.0 |
| 39 | 3.6 | 9.4 | 30.0 |
| 40 | 16.7 | 30.9 | 70.8 |
| 41 | 16.9 | 27.5 | 59.5 |
| Comp. Ex. 4 | 1.3 | 4.5 | 19.3 |
| Comp. Ex. 5 | 0.7 | 3.1 | 11.8 |

INDUSTRIAL APPLICABILITY

The external preparations of the present invention containing Aspirin can reserve stably Aspirin for a long term and is superior in transdermal absorption of Aspirin from skin.

What is claimed is:

1. A stable external preparation comprising Aspirin and at least one substance selected from the group consisting of an ester of an organic acid having 2 to 20 carbon atoms, a glyerol fatty acid ester, squalane, squalene and crotamiton.

2. The stable external preparation of claim 1 wherein the ester of an organic acid is an ester of myristic acid, lauric acid, oleic acid, sebacic acid, palmitic acid, isooctanoic acid, isostearic acid, acetic acid or adipic acid.

3. The stable external preparation claim 1 wherein the ester of an organic acid is an ester of myristic acid, oleic acid, sebacic acid, palmitic acid, isooctanoic acid, isostearic acid or adipic acid.

4. The stable external preparation wherein the esters of an organic acid are esters of myristic acid, oleic acid, sebacic acid and adipic acid.

5. The stable external preparation claim 1 wherein the glycerol fatty acid ester is soy bean oil, almond oil, sesame oil, triacetin, a middle chain-fatty acid triglyceride or glycerol triisooctanoic acid.

6. The stable external preparation of claim 1 wherein the glycerol fatty acid ester is soy bean oil, almond oil, sesame oil or a middle chain-fatty acid triglyceride.

7. The stable external preparation of claim 1, wherein said at least one substance is squalane.

* * * * *